(12) United States Patent
Kalkote et al.

(10) Patent No.: US 7,041,830 B2
(45) Date of Patent: May 9, 2006

(54) PROCESS FOR PREPARING (RS) 3-METHYL-1-(2-PIPERIDINYL PHENYL) BUTYL AMINE

(75) Inventors: Uttam Ramrao Kalkote, Pune (IN); Mukund Keshao Gurjar, Pune (IN); Shreerang Vidyadhar Joshi, Pune (IN); Suresh Mahadev Kadam, Pune (IN); Harish Kashinath Mondkar, Pune (IN)

(73) Assignee: Council of Scientific and Industrial Research, New Dehi (IN)

( * ) Notice: Subject to any disclaimer, the term of this patent is extended or adjusted under 35 U.S.C. 154(b) by 390 days.

(21) Appl. No.: 10/404,007

(22) Filed: Mar. 31, 2003

(65) Prior Publication Data

US 2004/0192921 A1    Sep. 30, 2004

(51) Int. Cl.
 *C07D 211/26*    (2006.01)
(52) U.S. Cl. ..................... 546/229; 546/237
(58) Field of Classification Search ............... 546/191, 546/229, 246, 237
See application file for complete search history.

(56) References Cited

OTHER PUBLICATIONS

Eiden et al. "Pyran derivatives. 107 . . . " CA 103:22242 (1985).*
Boehme et al. "Mechanism of condensation . . . " CA 103:6198 (1985).*

* cited by examiner

*Primary Examiner*—Celia Chang
(74) *Attorney, Agent, or Firm*—Ladas and Parry LLP

(57) ABSTRACT

The Present invention relates to a process for the preparation of (RS) 3-methyl-1-(2-piperidinyl phenyl) butyl amine of formula 1.

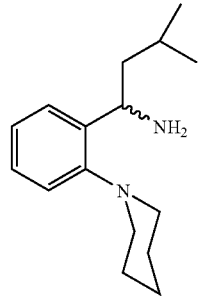

Formula 1

(RS) 3-Methyl-1-(2-piperidinyl phenyl) butyl amine having formula 1 is an important key intermediate for the synthesis of repaglinide of formula 2 an oral hypoglycemic agent.

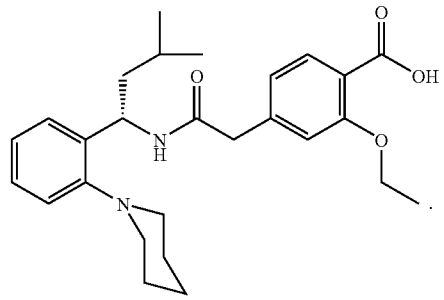

Formula 2

9 Claims, No Drawings

PROCESS FOR PREPARING (RS) 3-METHYL-1-(2-PIPERIDINYL PHENYL) BUTYL AMINE

FIELD OF THE INVENTION

The present invention relates to a process for the preparation of (RS) 3-methyl-1-(2-piperidinyl phenyl) butyl amine of formula 1.

Formula 1

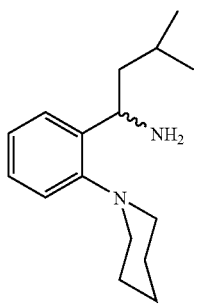

(RS) 3-Methyl-1-(2-piperidinyl phenyl butyl amine having formula 1 is an important key intermediate for the synthesis of repaglinide of formula 2 an oral hypoglycemic agent.

Formula 2

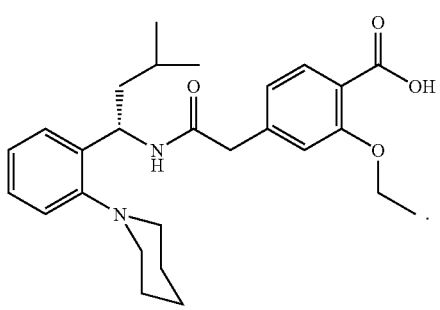

BACKGROUND OF THE INVENTION

Repaglinide (+) 2 ethoxy-4[N-{1-(2-piperidinophenyl)3-methyl-butyl}aminocarbonyl methyl]benzoicacid of formula 2 is from a class of hypoglycemic agents for type II non insulin dependant diabetes mellitus Hitherto known process for the preparation of (RS) 3-methyl-1-(2-piperidinyl phenyl butyl amine having formula 1 involves two methods as shown below Route 1 (J. Med. Chem. 1998, 41, 5219)

a. Heating a mixture of 2-halo bezonitrile, piperidine, and N-formyl piperidine at 160–170° C. to obtain 2-piperidino benzonitrle of formula 3.

Formula 3

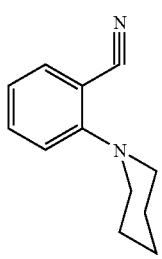

b. Grignard reaction: The reaction of i BuMgBr with 2-piperidino benzonitrile in THF solvent to obtain (3-methylbutyl)-(2-piperidino-phenyl)-ketimine having formula 4.

Formula 4

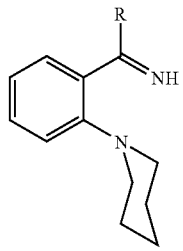

c. Hydrogenation of (3-methylbutyl)-(2-piperidino-phenyl)-ketimine of formula 4 in methanolic ammonia in presence of raney nickel at 80 C for 6 hrs to obtain (RS) 3-methyl-1-(2-piperidinyl phenyl butyl amine having formula 1

Formula 1

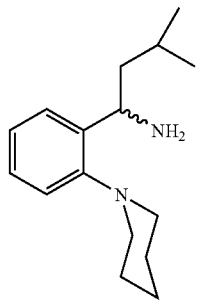

Route 2.

a. Heating a solution of 2-piperidino benzonitrile of formula 3 in formic acid in the presence of raney nickel to obtain 2-piperidino benzaldehyde of formula 5.

Formula 5

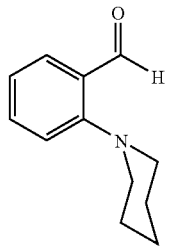

b. Hydrogenation of o-piperidino benzaldehyde of formula 5 in methanolic ammonia in the presence of raney nickel to obtain 2-piperidino benzylamine of formula 6.

Formula 6

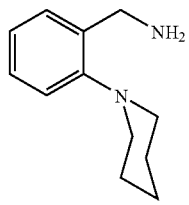

c. Condensation of 2-piperidino benzylamine of formula 6 with 2-piperidino benzaldehyde of formula 5 to obtain N-(2-piperidinobenzyl)-2-piperidino benzaldimine of formula 7.

Formula 7

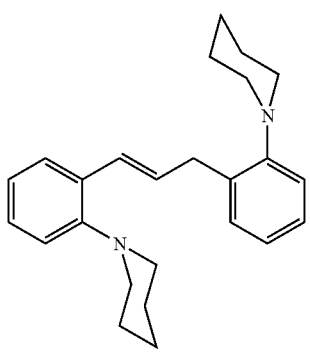

d. Alkylation of N-(2-piperidinobenzyl)-2-piperidino benzaldimine of formula 7 with 2-methylallyl chloride in presence of base i.e LDA to obtain (RS) 3-methyl-1-(2-piperidinyl phenyl) butyl amine having formula 1

Formula 1

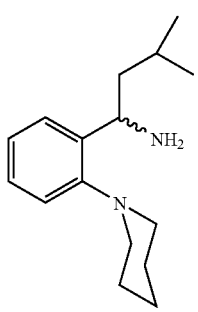

The prior art processes have following drawbacks.
1. Condensation of piperidine requires higher temperature.
2. Reduction of ketimine requires autoclave which is inconvenient on industrial scale.
3. The use of strong base i.e LDA reagent requires −80° C. which is also inconvenient on industrial scale.

OBJECTS OF THE INVENTION

The main object of the present invention is to provide a new process for the preparation of (RS) 3-methyl-1-(2-piperidinyl phenyl) butyl amine having formula 1 which obviates the drawbacks of the prior art processes and use cheaper and easily available chemicals.

SUMMARY OF THE INVENTION

Accordingly the present invention provides a new process for the preparation of (RS) 3-methyl-1-(2-piperidinyl phenyl) butyl amine having formula 1 which comprises Formula 1

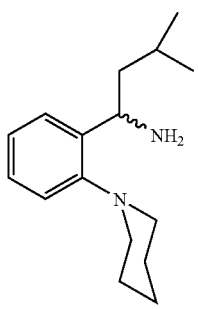

comprising oximation of a ketone of formula 10 with hydroxyl amine hydrochloride in an alcohol solvent at a temperature in the range of 60–80° C., removing the solvent by evaporation to obtain an oxime of formula 11

Formula 10

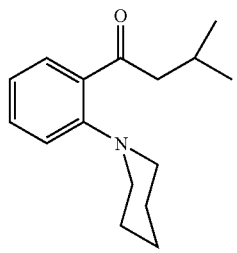

Formula 11

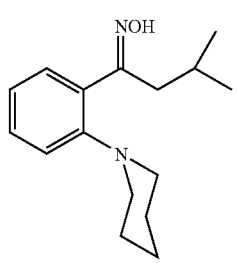

reducing the oxime of formula 11 with a reducing agent in an alcohol solvent at a temperature in the range of 40–60° C. for a time period in the range of 5–10 hrs, removing the solvent, extracting with ethyl acetate, washing with brine, removing the solvent by evaporation to obtain (RS) 3-methyl-1-(2-piperidinyl phenyl) butyl amine having formula 1

In one embodiment of the invention, the ketone of formula 10 is obtained by the addition of a Grignard reagent (RMgX) to 2-halobenzaldehyde in an organic solvent at a temperature in the range of 30–60° C. for a time period in the range of 2–8 hrs, quenching with brine solution, separating the solvent, removing the solvent by evaporation to obtain an alcohol of formula 12

Formula 12

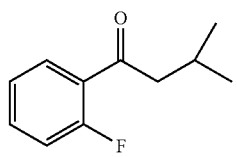

oxidizing the alcohol of formula 12 with an oxidizing reagent in an organic solvent at a temperature in the range of 30–40° C. for a time period in the range of 10–24 hrs, separating the solvent, evaporating the solvent to obtain ketone of formula 13

Formula 13

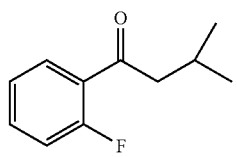

condensing piperidine with the ketone of formula 13 in the presence of potassium carbonate in organic solvent at a temperature in the range of 80–140° C. for a time period in the range of 5–10 hrs, separating the organic solvent, removing the solvent by evaporation to obtain ketone having formula 10.

Formula 10

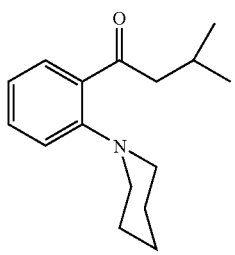

In another embodiment of the invention, the ketone of formula 10 is obtained by a reacting 2-halobenzaldehyde with piperidine in the presence of potassium carbonate in organic solvent at temperature ranging from 60–100° C., filtering, removing the solvent to obtain 2-piperidino benzaldehyde of formula 8

Formula 8

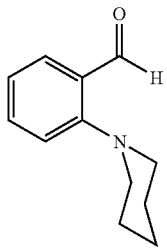

adding a Grignard reagent (RMgX) to 2-piperidino benzaldehyde of formula 8 in dry ether, stirring at 40° C. for a time period in the range of 2–6 hrs, quenching with brine solution, separating organic layer, evaporating the solvent to obtain an alcohol of formula 9

Formula 9

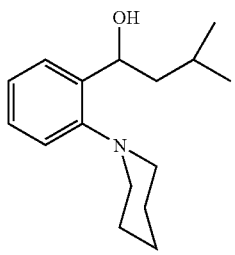

oxidizing the alcohol of formula 9 with an oxidizing agent in organic solvent to obtain ketone of formula 10.

Formula 10

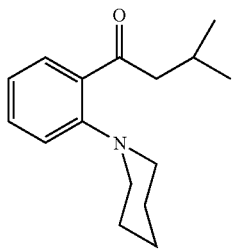

In another embodiment of the invention the organic solvent used for the condensation of piperidine is selected from the group consist of dimethyl formamide, toluene and xylene.

In another embodiment of the invention the organic solvent used for oxidation reaction is selected from dichloromethane and dichloroethane.

In another embodiment of the invention the organic solvent used for reduction is selected from ethyl alcohol and methyl alcohol.

In another embodiment of the invention the reducing agent used is selected from the group consisting of sodium borohydride, LiAlH$_4$, ammonium formate and sodium cyano borohydride.

In another embodiment of the invention the oxidizing agent used is selected from the group consisting of MnO$_2$, PCC, PDCC and Jones reagent.

DETAILED DESCRIPTION OF THE INVENTION

The process of the present invention is described herein below with references to the following example, which are illustrative only and should not be construed to unit the scope of the present invention in any manner.

EXAMPLE 1

Preparation of o-piperidino benzaldehyde (8)

A mixture of o-fluorobenzaldehyde (1.24 gm, 10 mmol), potassium carbonate (2.76 gm, 20 mmol), and piperidine (1.7 gm, 20 mmol) was refluxed in dry DMF for 6 hrs. After the completion of reaction DMF was distilled out at vaccum and 5 ml of water was added to the residue and extracted the product with ethyl acetate (10 ml×2). Organic layer was dried over sodium sulphate and evaporated the solvent to afford 1.8 gm of product (8) (90.5%) $^1$HNMR CDCl$_3$ (Spectrum 9): 1.68(m, 6H), 3.05(m, 4H), 7.05(m, 2H), 7.45(dd, 1H), 7.75(dd, 1H).

EXAMPLE 2

Preparation of 3-methyl-1-(2-piperidino phenyl)butylalcohol (9)

In a 3 necked round bottom flask (25 ml), equipped with a dropping funnel, reflux condenser and thermometer pocket, placed magnesium turnings (0.254 gm, 10.47 mmol) and flame dried the apparatus. Dry diethyl ether (10 ml.) was added to Mg. Turning, Isobutyl bromide (1.13 ml, 1.45 gm, 10.58 mmol) was taken in 2 ml of dry ether and added drop wise to the Mg turnings. As soon as ether starts boiling (in a few minutes) the reaction was cooled using ice-salt and continued the addition of isobutyl bromide. After complete addition of isobutyl bromide continued for another 20 minutes. o-piperidino benzaldehyde 8 (1.0 gm, 5.29 mmol) in 2 ml of ether was added drop wise at −10° C. After the completion of addition of 8 continued the stirring for 1 hr and the reaction was quenched with ice-cooled saturated ammonium chloride solution (5 ml), the solid separated is filtered off, the filtrate is extracted with ethyl acetate (10×2 ml) dried over sodium sulphate and concentrated to yield 1.36 gm of crude product. The crude product was chromatographed and obtained pure 9 (54.2%).

$^1$HNMR CDCl$_3$ (Spectrum 10): 0.96(d, 6H), 1.70(m, 9H), 2.88(m, 4H), 4.84(m, 1H), 7.14(m, 2H), 7.23(m, 2H).

EXAMPLE 3

Preparation of 3-methyl-1-(2-fluoro phenyl)butylalcohol (12)

In a 3 necked round bottom flask (100 ml), equipped with a dropping funnel reflux condenser and thermometer pocket, placed magnesium turnings (1.45 gm 0.0604 mole) and flame dried the apparatus. Dry diethyl ether (15 ml.) was added to Mg. Turning, Isobutyl bromide (6.57 ml, 8.28 gm, 0.0645 mole) was taken in 5 ml of dry ether and added drop wise to the Mg turnings. As soon as ether starts boiling (in a few minutes) the reaction was cooled using ice-salt and continued the addition of isobutyl bromide. After complete addition of isobutyl bromide continued for another 20 minutes. o-Fluro benzaldehyde (4.25 ml, 5.0 gm, 0.0403 mole) in 10 ml of ether was added drop wise at −10° C. (around ½ hr). After the completion of addition of fluoro benzaldehyde continued the stirring for 1 hr and the reaction was quenched with ice-cooled saturated ammonium chloride solution (30 ml), the solid separated is filtered off, the filtrate is extracted with ethyl acetate (20×1, 10×2 ml) dried over sodium sulphate and concentrated to yield 6.54 gm of crude product (GC showed area of 85% purity). The crude product on vacuum distillation gave 3.93 gm (54.2%) of pure 3-methyl-1-(2-fluoro phenyl)butylalcohol (12) and impure product ~2.87 gm containing 3-methyl-1-(2-fluoro phenyl)butylalcohol (12) 60% and byproduct (o-fluoro benzylalcohol) 40%. $^1$HNMR $CDCl_3$ (spectrum 11): 0.96(d, 6H), 1.55(m, 1H), 1.75(m, 2H), 1.95 (bs, 1H), 5.05(m, 1H), 7.0(m, 1H), 7.20(m, 2H), 7.45(m, 1H)

GC Conditions

| Column | HP1 |
| --- | --- |
| Temperature | 100° C. |
| o-Fluorobenzaldehyde | 0.61 RT |
| o-Fluorobenzylalcohol | 0.89 RT |
| 3-methyl-1-(2-fluoro phenyl)butylalcohol (12) | 4.07 RT |

EXAMPLE 4

Preparation of isobutyl-(2-fluoro-phenyl)-ketone (13)

In a round bottom flask (100 ml) was placed 3-methyl-1-(2-fluoro phenyl)butylalcohol 12 (1.85 gm, 0.0103 mole) and dichloromethae (35 ml). $MnO_2$ (12.52 gm) was added to it. The reaction mixture was stirred for 20 hrs. After the completion of reaction (monitored by TLC or GC), the reaction mire was filtered through cilite, the filtrate was concentrated under reduced pressure to yield 1.57 gm (86%) of isobutyl-(2-fluoro-phenyl)-ketone 13 (GC purity 95%). $^1$HNMR $CDCl_3$: (spectrum 12) 0.96(d, 6H), 2.30(m, 1H), 2.85(m, 2H), 7.15(m, 2H), 7.45(m, 1H), 7.85(m, 1H).

GC Conditions

| Column | HP-1 |
| --- | --- |
| Temp | 100° C. |
| Ketone 13 | 3.18 RT |

EXAMPLE 5

Preparation of isobutyl-(2-piperidino-phenyl)-ketone (10)

A mixture of isobutyl-(2-fluoro-phenyl)-ketone 13 (0.928 gm, 5 mmole), piperidine (0.645 gm, 7.82 mole) and potassium carbonate (1.08 gm, 7.82 mmole) in 4 ml of DMF was heated for 4 hrs at 120° C. After completion of the reaction (monitored by TLC), the reaction mixture was cooled and water (30 ml) was added to the reaction mixture and then extracted with ethyl acetate (1×15 ml, 2×7 ml). The combined organic layers were washed with a saturated ammonium chloride solution (2×15 ml) and subsequently dried over sodium sulphate. The solvent was removed under reduced pressure to obtain isobutyl-(2-piperidino-phenyl)-ketone 10 in 95% yield (GC showed 90% Purity). $^1$HNMR $CDCl_3$, (spectrum 13): 0.92(d, 6H), 1.60(m, 6H), 2.07(m, 1H), 2.95(m, 6H), 7.05(m, 2H). 7.35(m, 2H). IR (spectrum 14) (Neat): 2841, 1657(C=O), 1570, 1435, 1345, 738

GC Conditions

| Column | HP-1 |
| --- | --- |
| Temp | 100–200° C. (20° C./min) |
| Piperidino Ketone 10 | 5.88 RT |

EXAMPLE 6

Preparation of Oxime (11)

Hydroxylamine hydrochloride (2.27 gm, 0.0326 mole) was neutralized with ethanolic NaOH (0.652 gm of NaOH in 6 ml ethyl alcohol), isobutyl-(2-piperidino-phenyl)-ketone 10 (2 gm, 0.00816 mole) in 8 ml of ethyl alcohol was added and stirred the reaction mixture for 3 hrs at room temperature. Then evaporated the ethyl alcohol under vacuum, then water (30 ml) was added to it and extracted twice (2×10 ml) with ethyl acetate. The organic layer was dried over sodium sulphate and concentrated to obtain oxime 11 (2.07 gm, 97%, GC purity 93%) as solid. $^1$HNMR $CDCl_3$ (spectrum 15): 0.82(d, 6H), 0.95(m, 1H), 1.65(m, 8H), 2.92(m, 4H), 7.02(m, 2H), 7.22(m, 2H). IR (spectrum 16): 3239, 3237 (O—H), 2924, 2854, 2792, 1588(C=N), 1450, 753

GC Conditions

| Column | HP-1 |
| --- | --- |
| Temp | 100–200° C. (20° C./min) |
| Oxime 11 | 6.70 RT |

EXAMPLE 7

Preparation of (RS)-3-methyl-1-(2-(1-piperidinyl) phenyl)-butyl amine (1)

To a solution of $NiCl_2.6H_2O$ (2.66 gm, 0.0112 mole) in methanol (8 ml) was added oxime 11 (1.94 gm, 0.00746 mole) in methanol (8 m), cooled the reaction mixture and added $NaBH_4$ (2.55 gm, 0.067 mole) in 4 portions with stirring. After 10 min the black precipitate is filtered through cilite, the filtrate is concentrated in vacuum to ½ of its original volume and poured in to 100 ml, of water containing 6 ml of 30% $NH_4OH$ solution. Then extracted with ethyl acetate (1×15 ml, 2×10 ml), dried over sodium sulphate and on evaporation of the solvent gave crude amine 1 (1.366 gm, 76%, GC purity 95%). $^1$HNMR CDCl$_3$ (spectrum 17): 0.95(d, 6H), 1.65(m, 8H), 2.85(m, 4H), 3.25(bs, 2H), 4.55(t, 1H), 7.1(m, 2H0, 7.35(m, 2H). IR (spectrum 18) (34459, 3416 NH$_2$), 2859, 1653, 1590, 1450, 753

GC Conditions

| Column | HP-1 |
|---|---|
| Temp | 100–200° C. (20° C./min) |
| Amine 1 | 5.90 RT |

EXAMPLE 8

Methanol (100 ml), oxime 11 (11 gm) and Raney nickel from Kallina Industries (7 cc) were placed in pressure reactor and flushed with hydrogen, and the reaction was kept stirring with hydrogen pressure (50 psi) for 17 hrs. After complete reaction the catalyst was removed by filtration and solvent was removed under vacuum to yield amine 1 (10.4 gm, GC purity 87%)

We claim:

1. A process for the preparation of (RS) 3-methyl-1-(2-piperidinyl phenyl) butyl amine having formula 1 which comprises

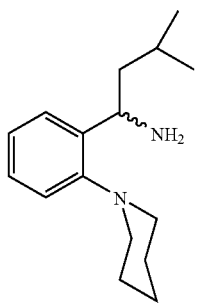

Formula 1 oximation of a ketone of formula 10 with hydroxyl amine hydrochloride in an alcohol solvent at a temperature in the range of 60–80° C., removing the solvent by evaporation to obtain an oxime of formula 11

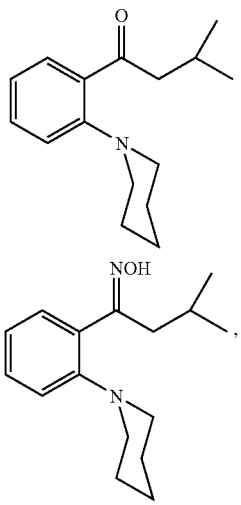

Formula 10

Formula 11 reducing the oxime of formula 11 with a reducing agent in an alcohol solvent at a temperature in the range of 40–60° C. for a time period in the range of 5–10 hrs, wherein the reducing agent is selected from the group consisting of sodium borohydride, LiAlH$_4$, ammonium formate and sodium cyano borohydride, removing the solvent, extracting with ethyl acetate, washing with brine, removing the solvent by evaporation to obtain the (RS) 3-methyl-1-(2-piperidinyl phenyl) butyl amine having formula 1.

2. A process as claimed in claim 1, wherein the ketone of formula 10 is obtained by the addition of a Grignard reagent to 2-halobenzaldehyde in an organic solvent at a temperature in the range of 30–60° C. for a time period in the range of 2–8 hrs, quenching with brine solution, separating the solvent, removing the solvent by evaporation to obtain an alcohol of formula 12

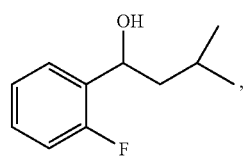

Formula 12 oxidizing the alcohol of formula 12 with an oxidizing reagent in an organic solvent at a temperature in the range of 30–40° C. for a time period in the range of 10–24 hrs, wherein the oxidizing agent is selected from the group consisting of MnO$_2$PCC, PDCC and Jones reagent, separating the solvent, evaporating the solvent to obtain ketone of formula 13

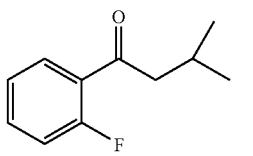

Formula 13 condensing piperidine with the ketone of formula 13 in the presence of potassium carbonate in organic solvent at a temperature in the range of 80–140° C. for a time period in the range of 5–10 hrs, separating the organic solvent, and removing the solvent by evaporation to obtain ketone having formula 10

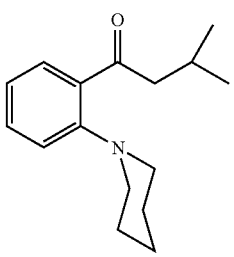

Formula 10

3. A process as claimed in claim 1, wherein the ketone of formula 10 is obtained by a reacting 2-halobenzaldehyde with piperidine in the presence of potassium carbonate in organic solvent at temperature ranging from 60–100° C., filtering, removing the solvent to obtain 2-piperidino benzaldehyde of formula 8

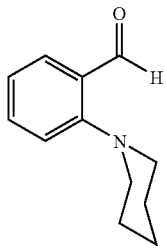

Formula 8 adding a Grignard reagent to 2-piperidino benzaldehyde of formula 8 in dry ether, stirring at 40° C. for a time period in the range of 2–6 hrs, quenching with brine solution, separating organic layer, evaporating the solvent to obtain an alcohol of formula 9

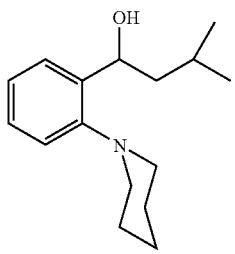

Formula 9 oxidizing the alcohol of formula 9 with an oxidizing agent in organic solvent to obtain ketone of formula 10, wherein the oxidizing agent is selected from the group consisting of $MnO_2$, PCC, PDCC and Jones reagent

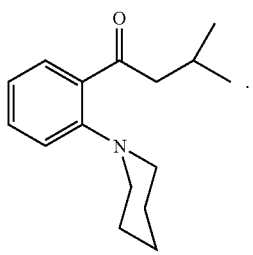

Formula 10

4. A process as claimed in claim 2, wherein the organic solvent for the condensation of piperidine is selected from the group consisting of dimethyl formamide, toluene and xylene.

5. A process as claimed in claim 3, wherein the organic solvent for oxidation reaction is selected from the group consisting of dichloromethane and dichloroethane.

6. A process as claimed in claim 1, wherein the organic solvent for reduction is selected from the group consisting of ethyl alcohol and methyl alcohol.

7. A process as claimed in claim 1, wherein the reducing is carried out in the presence of nickel chloride.

8. A process for the preparation of (RS) 3-methyl-1-(2-piperidinyl phenyl) butyl amine having formula 1 comprising

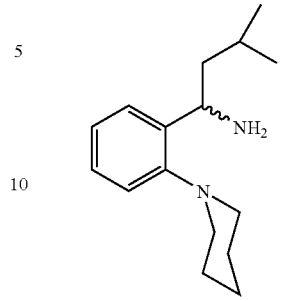

Formula 1 a. reacting 2-halobenzaldehyde with piperidine in the presence of base in organic solvent at temperature ranging from 60–100° C. to obtain 2-piperidino benzaldehyde of formula 8

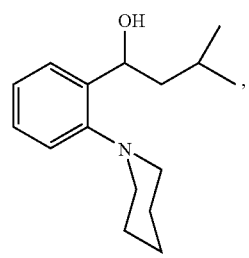

Formula 8 b. adding Grignard reagent to 2-piperidino benzaldehyde of formula 8 in organic solvent for a period ranging from 2–6 hrs to obtain alcohol product having formula 9

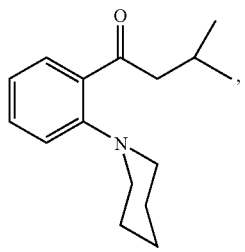

Formula 9 c. oxidation of alcohol of formula 9 with oxidizing agent in organic solvent to obtain ketone of formula 10, wherein the oxidizing agent is selected from the group consisting of $MnO_2$ PCC, PDCC and Jones reagent Formula 10 d. oximation of ketone 10 with hydroxyl amine hydrochloride in organic solvent at temperature ranging from 60–80° C. to obtain oxime having formula 11

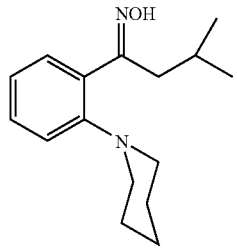

Formula 11 e. reduction of oxime of formula 11 with reducing agent in organic solvent ranging from 40–60 C. for the period ranging from 5–10 hrs to obtain the (RS) 3-methyl-1-(2-piperidinyl phenyl) butyl amine having formula 1, wherein the reducing agent is selected from the group consisting of sodium borohydride, LiAlH$_4$, ammonium formate and sodium cyano borohydride.

9. A process for the preparation of (RS) 3-methyl-1-(2-piperidinyl phenyl) butyl amine having formula 1

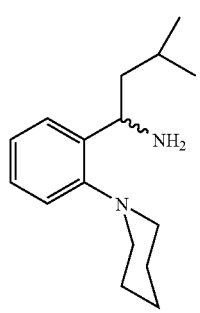

Formula 1 comprising a. addition of Grignard reagent (RMgx) with 2-halobenzaldehyde in organic solvent at temperature ranging from 30–60°C. for a period ranging from 2–8 hrs to obtain alcohol of formula 12

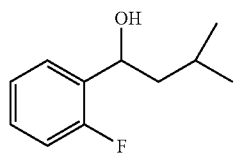

Formula 12 b. oxidation of alcohol of formula 12 with oxidizing reagent in organic solvent at temperature ranging from 30–40° C. for a period rang from 10–24 hrs to obtain ketone of formula 13, wherein the oxidizing agent is selected from the group consisting of MnO$_2$ PCC, PDCC and Jones reagent

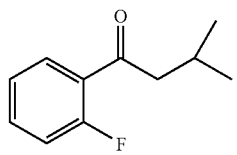

Formula 13 c. condensation of piperidine with ketone of formula 13 in the presence of potassium carbonate in organic solvent ranging from 80–140° C. for a period ranging from 5–10 hrs to obtain ketone having formula 10

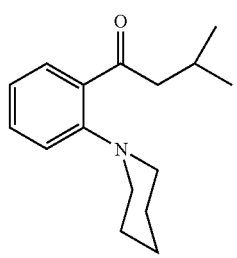

Formula 10 d. oximation of ketone of formula 10 with hydroxyl amine hydrochloride in organic solvent at temperature ranging from 60–80° C. to obtain oxime having formula 11

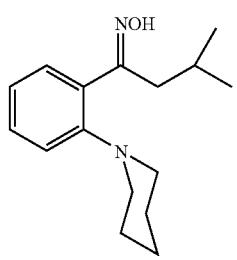

Formula 11 e. reduction of oxime of formula 11 with reducing agent in organic solvent at a temperature ranging from 40–60°C. for a period ranging from 5–10 hrs to obtain the (RS) 3-methyl-1-(2-piperidinyl phenyl) butyl amine having formula 1, wherein the reducing agent is selected from the group consisting of sodium borohydride, LiAlH$_4$, ammonium formate and sodium cyano borohydride.

* * * * *